United States Patent [19]

Brown

[11] 4,378,012
[45] Mar. 29, 1983

[54] ENDO-TRACHEAL TUBE HOLDER

[76] Inventor: Doland Brown, 2005 Parkdale Ave., Toledo, Ohio 43607

[21] Appl. No.: 260,219

[22] Filed: May 4, 1981

[51] Int. Cl.³ .............................................. A61M 25/02
[52] U.S. Cl. ...................... 128/207.17; 128/DIG. 26; 128/207.14; 604/77
[58] Field of Search ...................... 128/200.26, 207.14, 128/207.15, 207.17, 207.18, 349 B, 349 R, DIG. 26, 348

[56] References Cited

U.S. PATENT DOCUMENTS

| 3,146,778 | 9/1964 | Krawiec | 128/348 |
| 3,161,199 | 12/1964 | Shaw et al. | 128/DIG. 26 |
| 3,430,300 | 3/1969 | Doan | 128/DIG. 26 |
| 3,542,321 | 11/1970 | Kahabka | 128/DIG. 26 |
| 3,765,421 | 10/1973 | Poprik | 128/DIG. 26 |
| 3,774,616 | 11/1973 | White et al. | 128/DIG. 26 |
| 3,927,676 | 12/1975 | Schultz | 128/207.17 |
| 4,096,863 | 6/1978 | Kaplan et al. | 128/DIG. 26 |
| 4,326,515 | 4/1982 | Shaffer et al. | 128/DIG. 26 |
| 4,331,143 | 5/1982 | Foster | 128/207.17 |

OTHER PUBLICATIONS

Schmerk et al., *The Western Journal of Medicine*, Feb. 1976, pp. 172–173.
Copy of instruction brochure for the device "Tube Tamer" manufactured by Kinetic Concepts.

*Primary Examiner*—Henry J. Recla
*Attorney, Agent, or Firm*—Wilson, Fraser, Barker & Clemens

[57] ABSTRACT

An endo-tracheal tube holder comprises a web or strap including separable fasteners at the ends of flexible material of the web for adjusting the size of a loop formed by the web, and an adjustable tube retaining means secured to the web.

3 Claims, 3 Drawing Figures

FIG. I

U.S. Patent  Mar. 29, 1983  Sheet 2 of 2  4,378,012

ENDO-TRACHEAL TUBE HOLDER

BACKGROUND OF THE INVENTION

1. Field of the Invention

The invention relates to an apparatus for securely and conveniently holding an endo-tracheal tube in position in relation to a patient's mouth, during a medical procedure.

2. Description of the Prior Art

Prior endo-tracheal tube holders have suffered from a lack of continuous adjustability and of ease of operation. For example, one type of tube holder includes a plastic mouthpiece partially insertable within the patient's mouth. The mouthpiece includes a hole formed therein for receiving the endo-tracheal tube, and a spring clamp for retaining the tube. A strap is attached to the mouthpiece and adapted to extend around the patient's head or neck. Typically, the strap includes a buckle, by means of which the length of the strap is adjustable in increments.

Such tube holders operate effectively to maintain endo-tracheal tubes in position, but suffer from several drawbacks. Such devices are unnecessarily complicated and expensive. Furthermore, the incrementally adjustable strap buckle does not in all cases provide the desired secure attachment, as well as patient comfort. To provide some tolerance in adjustability, straps have been made elastic to a greater or lesser degree, but elastic straps offer less control, and are more expensive to manufacture. Finally, tube holders including formed plastic mouthpieces are somewhat bulky, causing problems and storage and inventory.

There is a need therefore for a simple endo-tracheal tube holder, which is inexpensive to manufacture. Other desired features include a compact size to facilitate storage, and ease of use. Finally, as with all medical equipment, reliability is of utmost importance.

SUMMARY OF THE INVENTION

It is, therefore, an object of the invention to provide an endo-tracheal tube holder including a strap and fastener permitting a continuous, rather than an incremental, adjustment of the length of the loop formed by the strap. It is another object of the present invention to provide such an endo-tracheal tube holder in which the clamp means for the tube comprises a simple, one-piece adjustable loop of thermoplastic material.

A tube holder according to the invention comprises a web or strap typically formed of a strong, substantially inelastic flexible woven fabric. The web is of a size suitable for extending around the jaw and behind the upper neck of a patient. The two free ends of the web include fasteners which are engagable at any point throughout a predetermined range of overlap of the strap ends of the web. When the web is placed in position around a patient's head, the ends are overlapped to form a loop which is continuously adjustable in length to securely position the endo-tracheal tube without undue constriction.

A tube retaining means or clamp including a small loop of thermoplastic material is secured to the web intermediate the ends thereof. The loop of the retaining means is also adjustable in length, to securely grip the endo-tracheal tube.

BRIEF DESCRIPTION OF THE DRAWINGS

The above objects and advantages of the invention will become readily apparent to one skilled in the art from reading the following detailed description of an embodiment of the invention, when considered in light of the accompanying drawings, in which.

DESCRIPTION OF THE PREFERRED EMBODIMENT

Figure 1:
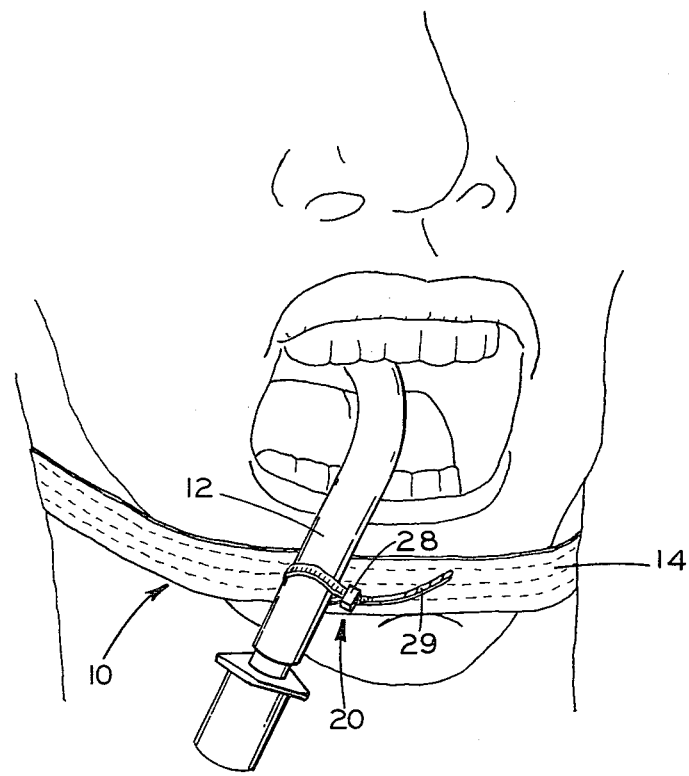
FIG. 1 is a perspective view of an endo-tracheal tube holder according to the invention in operating position on a patient.
Figure 2:
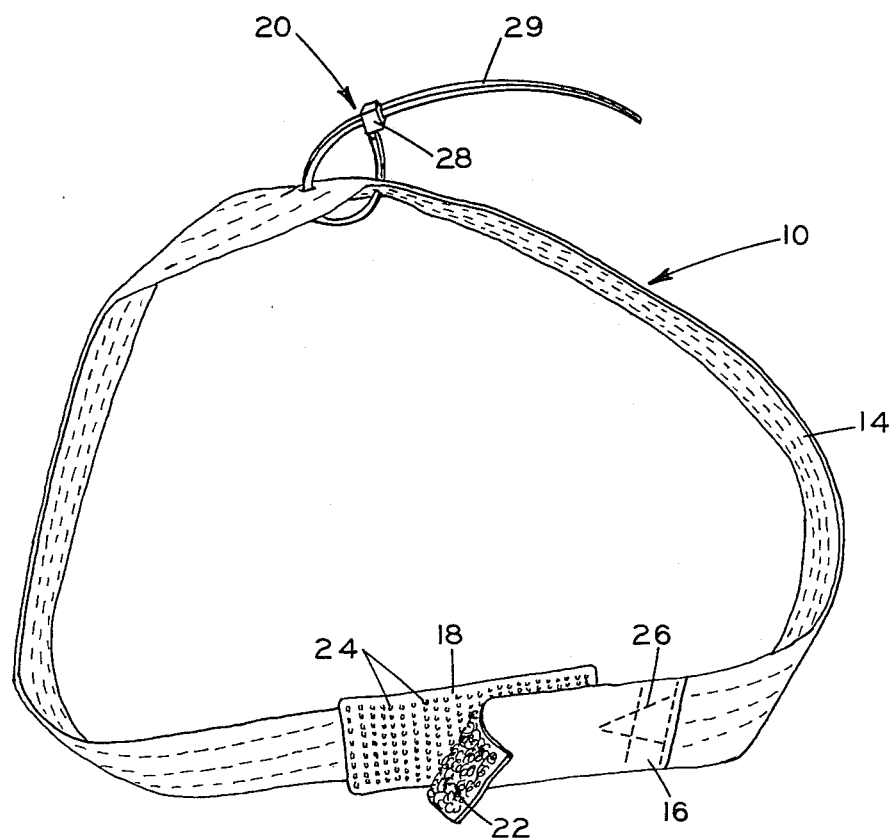
FIG. 2 is a perspective view of the endo-tracheal tube holder strap illustrated in FIG. 1.

Referring to FIG. 1, an endo-tracheal tube holder 10 is illustrated in operative position on a patient's head, retaining an endo-tracheal tube 12 in the appropriate position. As best seen in FIG. 2, the tube holder 10 includes a web or strap 14, fasteners 16 and 18 on respective ends of the strap 14, and a tube retaining means or clamp 20 secured to the strap 14.

The strap 14 is preferably formed from a strong, flexible, woven fabric, having minimal stretch. For proper fitting around a patient's neck and jaw, as illustrated in FIG. 1, the strap 14 is typically of a length of the range of approximately 50 centimeters. The length of the loop formed by the strap 14 is preferably adjustable by varying the extent of the overlap of the ends, within a range of approximately 35 to 50 centimeters.

The fasteners 16 and 18 provide this necessary adjustability. The fastener 16 comprises a fabric strip having a pile nap surface 22 including a myriad of looped threads. The fastener 18 comprises a strip having a plurality of small hooks formed of thermoplastic material, engagable with the pile surface of the fastener 16. Such fasteners are commercially available, and marketed under the trademark Velcro. The fasteners 16 and 18 are secured to opposite ends of the strap 14, preferably by stitching 26.

Figure 3:
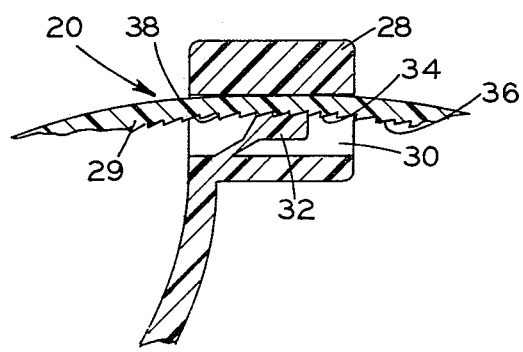
FIG. 3 is an enlarged scale, sectional view of the adjustable tube clamping means.

The tube retaining means or clamp 20 includes an integrally formed, elongate thermoplastic body portion 29 of a size capable of being formed into a loop of a desired size. A illustrated in detail in the sectional veiw of FIG. 3, one end of the body portion 29 terminates in a small housing 28 having a channel 30 formed therethrough to receive the opposite end of the body portion 29. The housing 28 further includes an integrally formed, resilient pawl 32 engagable with an elongate array of serrations 34 formed on one surface of the body portion 29. The serrations 34 include inclined camming surfaces 36 so formed to cam past the pawl 32. The serrations 36 also include detent surfaces 38 which are positively engagable with the pawl 32. In effect, the body portion 29 and the housing 28 cooperate to form a rack and ratchet mechanism permitting relative movement in only one direction. The one end of the body portion 29 may be freely pulled through the channel 30 in the direction to decrease the dimension of the loop so formed and tighten the same onto an endo-tracheal tube 12. The pawl 32 and serrations 36 cooperate to militate against retrograde movement and thereby prevent the loosening of the clamp 20 during use of the tube holder 10.

The clamp 20 is preferably secured to the strap 14 by insertion of the body portion 29 through aperture means 40 formed at appropriate locations in the strap 14, prior to forming the loop of the clamp 20. The aperture means 40 are longitudinally spaced and centrally located between the longitudinal edges of the strap 14.

To use the endo-tracheal tube holder 10, the strap 14 is placed around the chin and the base of a patient's head, as illustrated in FIG. 1. The fasteners 16 and 18 are pulled to an overlapping relationship providing a snug fit of the strap 14 around the patient. Manual pressure on the fasteners 16 and 18 is sufficient to assure engagement of the hooks 24 with the pile surface 22, and thereby secure the strap 14 in position. To provide for the desired amount of adjustability, the fastener 16 may have a length of approximately 10 to 15 centimeters, the fastener 18 being engagable at any location thereon.

An endo-tracheal tube 12 can then be rapidly and reliably fixed in place relative to the strap 14 and the patient by placing it within the loop of the clamp 20, and tightening the clamp 20 thereon by pulling the free end of the serrated strip 29.

The endo-tracheal tube holder 10 thus described offers several important advantages. The fasteners 16 and 18 permit continuous adjustment of the length of the loop of the strap 14. Manipulation of the fasteners 16 and 18 is simple in comparison with other fasteners such as the buckle type, for example. Release and readjustment of the fasteners 16 and 18 can be readily effected merely by pulling the fastener 16 away from the fastener 18, then repositioning and again pressing together the two fasteners 16 and 18. The clamp 20 also offers a simple and reliable means for holding an endo-tracheal tube, in comparison with bulkier, less easily manipulated spring-type clamps. Finally, the entire tube holder apparatus 10 can be inexpensively manufactured from commercially available components and is expendable.

In accordance with the provision of the patent statutes, the principle and mode of operation of the apparatus have been explained and what is considered to represent its best embodiment has been illustrated and described. It should, however, be understood that the invention may be practiced otherwise than as specifically illustrated and described without departing from its spirit or scope.

What is claimed is:

1. An endo-tracheal tube holder comprising an elongate flexible web having front and rear surfaces and opposite ends adapted to encircle a patient's neck and jaw; separable fastening means on the ends of said web for joining the ends thereof to form a loop, said fastening means permitting continuous adjustment of the length of the loop so formed; aperture means formed through said flexible web intermediate the ends of said web and retaining means for retaining an endotracheal tube including a body portion of flexible material having opposite ends extending through said aperture means formed through said flexible web and secured together to form a retaining loop at the front surface thereof, and means permitting tightening of said retaining loop by relative movement of the ends thereof in a single direction to prevent loosening thereof.

2. The tube holder defined in claim 1 wherein said fastening means includes a fastener member at one end of said web having a fabric with a pile surface, and a fastener member at the other end of said web including a plurality of hooks separably engagable with said fabric pile surface.

3. The tube holder defined in claim 2 wherein said tube retaining means is formed of a flexible plastic material.

* * * * *